US012629266B2

(12) United States Patent
Shulaw

(10) Patent No.: US 12,629,266 B2
(45) Date of Patent: May 19, 2026

(54) ORTHOPAEDIC SURGICAL INSTRUMENT FOR EXTRACTING A FEMORAL STEM COMPONENT IN A HIP REPLACEMENT SURGICAL PROCEDURE AND METHOD OF USING THE SAME

(71) Applicant: DePuy Synthes Products, Inc., Raynham, MA (US)

(72) Inventor: Cory A. Shulaw, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 345 days.

(21) Appl. No.: 18/127,994

(22) Filed: Mar. 29, 2023

(65) Prior Publication Data

US 2024/0325168 A1     Oct. 3, 2024

(51) Int. Cl.
*A61F 2/46* (2006.01)

(52) U.S. Cl.
CPC .... *A61F 2/4607* (2013.01); *A61F 2002/4619* (2013.01); *A61F 2002/4627* (2013.01); *A61F 2002/4628* (2013.01)

(58) Field of Classification Search
CPC .................................................. A61F 2/4607
See application file for complete search history.

(56) References Cited

U.S. PATENT DOCUMENTS

| | | | | |
|---|---|---|---|---|
| 4,993,410 | A | * | 2/1991 | Kimsey ................. A61F 2/4607 606/100 |
| 5,534,006 | A | * | 7/1996 | Szabo ................... A61F 2/4607 606/100 |

| | | | |
|---|---|---|---|
| 6,228,091 | B1 | 5/2001 | Lombardo |
| 6,663,636 | B1 | 12/2003 | Lin |
| 8,393,409 | B2 | 3/2013 | Pedicini |
| 8,602,124 | B2 | 12/2013 | Pedicini |
| 8,695,726 | B2 | 4/2014 | Pedicini |
| 8,936,105 | B2 | 1/2015 | Pedicini |
| 8,936,106 | B2 | 1/2015 | Pedicini |
| 9,901,354 | B2 | 2/2018 | Pedicini |
| RE46,954 | E | 7/2018 | Pedicini |
| RE46,979 | E | 8/2018 | Pedicini |
| 10,342,591 | B2 | 7/2019 | Pedicini |

(Continued)

FOREIGN PATENT DOCUMENTS

| | | |
|---|---|---|
| DE | 202006012836 U1 | 10/2006 |
| DE | 202008017199 U1 | 3/2009 |

(Continued)

OTHER PUBLICATIONS

Shukla Medical Universal Orthopedic Extraction Technologies, Shukla Hip Universal Hip Implant Extraction Solution and Shukla Mod Hip v1, Surgical Technique Guide Systems 5 and 6 of 15, Jul. 1, 2020, 16 pages.

(Continued)

*Primary Examiner* — David W Bates
(74) *Attorney, Agent, or Firm* — Barnes & Thornburg LLP

(57) ABSTRACT

An orthopaedic surgical instrument for extracting an implanted femoral stem component includes a clamping jaw configured to the clamp the femoral component in the instrument's extraction loop. A leaf spring applies a spring bias to the clamped femoral component. A method of using an orthopaedic surgical instrument to extract an implanted femoral component is also disclosed.

19 Claims, 7 Drawing Sheets

(56)                References Cited

U.S. PATENT DOCUMENTS

| | | | |
|---|---|---|---|
| 10,381,696 | B2 | 8/2019 | Pedicini |
| 10,420,567 | B2 | 9/2019 | Pedicini |
| 10,446,895 | B2 | 10/2019 | Pedicini |
| 10,603,050 | B2 | 3/2020 | Pedicini |
| RE47,963 | E | 4/2020 | Pedicini |
| RE47,997 | E | 5/2020 | Pedicini |
| RE48,184 | E | 9/2020 | Pedicini |
| RE48,251 | E | 10/2020 | Pedicini |
| RE48,387 | E | 1/2021 | Pedicini |
| RE48,388 | E | 1/2021 | Pedicini |
| 10,912,597 | B2 | 2/2021 | Pedicini |
| 11,399,961 | B2 * | 8/2022 | Gosik-Wolfe ........ A61F 2/4603 |
| 2006/0200162 | A1 * | 9/2006 | Farling ................ A61B 17/157 606/88 |
| 2007/0167952 | A1 * | 7/2007 | Burgi ................ A61B 17/1666 606/99 |
| 2007/0173856 | A1 | 7/2007 | Parker |
| 2008/0221576 | A1 * | 9/2008 | Keller .................. A61F 2/4607 606/151 |
| 2008/0262503 | A1 * | 10/2008 | Muller .................. A61F 2/4612 606/99 |
| 2010/0121331 | A1 | 5/2010 | Sharp et al. |
| 2013/0226186 | A1 | 8/2013 | Burgi |
| 2014/0121650 | A1 | 5/2014 | Thomsen et al. |
| 2014/0207123 | A1 * | 7/2014 | Mueller ................ A61F 2/4607 606/1 |
| 2014/0207200 | A1 | 7/2014 | Kerboul et al. |
| 2016/0135963 | A1 | 5/2016 | Kerboul et al. |
| 2016/0213492 | A1 | 7/2016 | Castello et al. |
| 2017/0027715 | A1 | 2/2017 | Huang |
| 2017/0304078 | A1 | 10/2017 | Chenaux |
| 2018/0042734 | A1 * | 2/2018 | Slater .................... A61F 2/4607 |
| 2018/0055552 | A1 | 3/2018 | Pedicini |
| 2018/0055553 | A1 | 3/2018 | Pedicini |
| 2018/0055554 | A1 | 3/2018 | Pedicini |
| 2018/0338751 | A1 | 11/2018 | Pedicini |
| 2019/0183554 | A1 | 6/2019 | Pedicini |
| 2019/0223889 | A1 | 7/2019 | Pedicini |
| 2019/0282286 | A1 | 9/2019 | Pedicini |
| 2019/0305394 | A1 | 10/2019 | Pedicini |
| 2020/0197028 | A1 | 6/2020 | Pedicini |
| 2021/0315713 | A1 * | 10/2021 | Keach .................... A61B 17/92 |
| 2022/0313336 | A1 * | 10/2022 | Zapari .................. B25D 17/005 |
| 2022/0354559 | A1 * | 11/2022 | Lashure ................. A61B 17/92 |
| 2022/0354560 | A1 * | 11/2022 | Lashure ................. A61B 17/92 |
| 2023/0000644 | A1 * | 1/2023 | Kiska .................... A61F 2/4603 |
| 2024/0307193 | A1 * | 9/2024 | Keach .................... A61F 2/4607 |

FOREIGN PATENT DOCUMENTS

| | | | | |
|---|---|---|---|---|
| DE | 202018103170 | U1 * | 6/2018 | .......... A61F 2/4607 |
| EP | 1832248 | A2 | 9/2007 | |
| EP | 2777551 | A1 | 9/2014 | |
| WO | 2023278898 | A1 | 1/2023 | |

OTHER PUBLICATIONS

International Search Report and Written Opinion for International Application No. PCT/IB2024/052648, Jun. 18, 2024, 17 pages.

* cited by examiner

ORTHOPAEDIC SURGICAL INSTRUMENT FOR EXTRACTING A FEMORAL STEM COMPONENT IN A HIP REPLACEMENT SURGICAL PROCEDURE AND METHOD OF USING THE SAME

TECHNICAL FIELD

The present disclosure relates generally to orthopaedic instruments for use in the performance of an orthopaedic joint replacement procedure, and more particularly to orthopaedic surgical instruments for use in the performance of a hip replacement procedure.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is installed in the intramedullary canal of the patient's femur and a spherically-shaped head component that bears against the patient's acetabulum or a prosthetic replacement acetabular cup.

Typical joint arthroplasty surgical procedures include impaction of surgical instruments (e.g., insertion/extraction instruments, broaches, or other cutting tools) and/or prosthetic implants into the patient's bone. In some surgical procedures, such as revision surgical procedures, it is necessary to remove a previously implanted femoral stem component. In such a case, an extraction instrument is impacted by the surgeon to assert an extraction force on the femoral stem component to extract it from the patient's femur. Historically, impaction has been performed by an orthopaedic surgeon manually striking a surgical instrument using a surgical mallet or hammer.

Certain automated surgical impactors are capable of performing a series of percussive impacts that each provide a controlled amount of impaction force. An automated surgical impactor may be used with one or more adapters to connect to various surgical instruments and/or implants.

SUMMARY

According to one aspect, an orthopaedic surgical instrument for extracting a femoral stem component during an orthopaedic hip replacement surgical procedure on a patient's femur includes an elongated body having a connector formed in a proximal end of the elongated body that is configured to fit into the chuck of an automated surgical impactor. The elongated body also has an extraction loop formed in its distal end. The extraction loop has a bore that extends through the elongated body and is configured to receive a neck of the femoral stem component therein. The instrument also includes both a locking lever that has a pivot end that is pivotally coupled to the elongated body and an opposite latch end, and a clamping jaw that is slidably coupled to the elongated body. The clamping jaw is movable between a clamped position in which the clamping jaw is extended toward the extraction loop, and a released position in which the clamping jaw is retracted away from the extraction loop. A threaded drive assembly is operatively coupled to the clamping jaw and is operable to move the clamping jaw between its clamped position and its released position. A leaf spring of the instrument has a first end that is pivotally coupled to the locking lever and a second end that is coupled to the clamping jaw.

In an embodiment, the threaded drive assembly includes a drive screw rotatably coupled to the elongated body and a drive link slidably coupled to the elongated body. The drive link is operatively coupled to the clamping jaw. The drive screw has a socket defined in its proximal end and a threaded shaft extending distally away from the socket. The drive link has a threaded bore formed therein, with the threaded shaft of the drive screw being positioned in the threaded bore. Rotation of the drive screw in a first direction causes the drive link to be moved in the direction toward the extraction loop, whereas rotation of the drive screw in a second, opposite direction causes the drive link to be moved in the direction away from the extraction loop.

The instrument may also include a pushbutton catch coupled to the elongated body. In such an embodiment, the locking lever is movable between an unlocked position in which the latch end is spaced apart from the elongated body and a locked position in which the latch end is captured by the pushbutton catch.

The instrument may also include a compression spring positioned between the locking lever and the elongated body. The compression spring biases the locking lever into its unlocked position.

In an embodiment, the leaf spring asserts a spring bias on the neck of the femoral component when the neck of the femoral component is positioned in the extraction loop and the locking lever is positioned in its locked position.

In an embodiment, the clamping jaw asserts a clamping force on the neck of the femoral component when the neck of the femoral component is positioned in the extraction loop and the clamping jaw is positioned in its clamped position.

The second end of the leaf spring may be pivotally coupled to the clamping jaw. Alternatively, the instrument may include a knuckle link pivotally coupled to the elongated body with the second end of the leaf spring being pivotally coupled to a first end of the knuckle link. In such an embodiment, a second end of the knuckle link is coupled to the clamping jaw.

According to another aspect, an orthopaedic surgical instrument for extracting a femoral stem component during an orthopaedic hip replacement surgical procedure on a patient's femur includes an elongated body having a connector formed in a proximal end of the elongated body that is configured to fit into the chuck of an automated surgical impactor. The elongated body also has an extraction loop formed in its distal end. The extraction loop has a bore that extends through the elongated body and is configured to receive a neck of the femoral stem component therein. The instrument also includes both a locking lever that has a pivot end that is pivotally coupled to the elongated body and an opposite latch end, and a drive link slidably coupled to the elongated body. The drive link is movable within the elongated body in a direction toward, and a direction away from, the extraction loop. A connecting link has a first end that is pivotally coupled to the locking lever and a second end that is pivotally coupled to the drive link. A clamping jaw is slidably coupled to the elongated body. The clamping jaw is movable between a clamped position in which the clamping jaw is extended toward the extraction loop, and a released position in which the clamping jaw is retracted away from the extraction loop. A leaf spring has a first end that is pivotally coupled to the locking lever and a second end that is coupled to the clamping jaw. In such an arrangement, movement of the drive link in the direction toward the extraction loop causes the clamping jaw to be positioned in its clamped position, and movement of the drive link in the direction away from the extraction loop causes the clamping jaw to be positioned in its released position.

The instrument may also include a drive screw rotatably coupled to the elongated body. The drive screw has a socket defined in its proximal end and a threaded shaft extending distally away from the socket. The drive link has a threaded bore formed therein, with the threaded shaft of the drive screw being positioned in the threaded bore. Rotation of the drive screw in a first direction causes the drive link to be moved in the direction toward the extraction loop, whereas rotation of the drive screw in a second, opposite direction causes the drive link to be moved in the direction away from the extraction loop.

In an embodiment, the locking lever has a slot formed therein. The first end of the leaf spring and the first end of the connecting link are coupled to one another by a pivot pin that translates within the slot of the locking lever.

The instrument may also include a pushbutton catch coupled to the elongated body. In such an embodiment, the locking lever is movable between an unlocked position in which the latch end is spaced apart from the elongated body and a locked position in which the latch end is captured by the pushbutton catch.

The instrument may also include a compression spring positioned between the locking lever and the elongated body. The compression spring biases the locking lever into its unlocked position.

In an embodiment, the leaf spring asserts a spring bias on the neck of the femoral component when the neck of the femoral component is positioned in the extraction loop and the locking lever is positioned in its locked position.

In an embodiment, the clamping jaw asserts a clamping force on the neck of the femoral component when the neck of the femoral component is positioned in the extraction loop and the clamping jaw is positioned in its clamped position.

The second end of the leaf spring may be pivotally coupled to the clamping jaw. Alternatively, the instrument may include a knuckle link pivotally coupled to the elongated body with the second end of the leaf spring being pivotally coupled to a first end of the knuckle link. In such an embodiment, a second end of the knuckle link is coupled to the clamping jaw.

According to another aspect, a method of extracting an implanted femoral stem component during performance of an orthopaedic hip replacement surgical procedure on a patient's femur includes positioning an extraction loop of an orthopaedic surgical instrument around a neck of the femoral stem component. A threaded drive assembly of the orthopaedic surgical instrument is then operated to move a clamping jaw into contact with the neck of the femoral stem component. Thereafter, a locking lever of the orthopaedic surgical instrument is moved into a locked position so as to apply a spring bias on the neck of the femoral stem component with a leaf spring. A connector of the orthopaedic surgical instrument is coupled to a chuck of an automated surgical impactor, and the automated surgical impactor is then operated to apply an extraction force on the femoral stem component.

In an embodiment, a drive screw of the threaded drive assembly is rotated so as to move the clamping jaw into contact with the neck of the femoral stem component.

In an embodiment, a latch end of the locking lever is captured in a pushbutton catch so as to retain the locking lever in its locked position.

BRIEF DESCRIPTION OF THE DRAWINGS

The detailed description particularly refers to the following figures, in which.

DETAILED DESCRIPTION OF THE DRAWINGS

Figure 1:
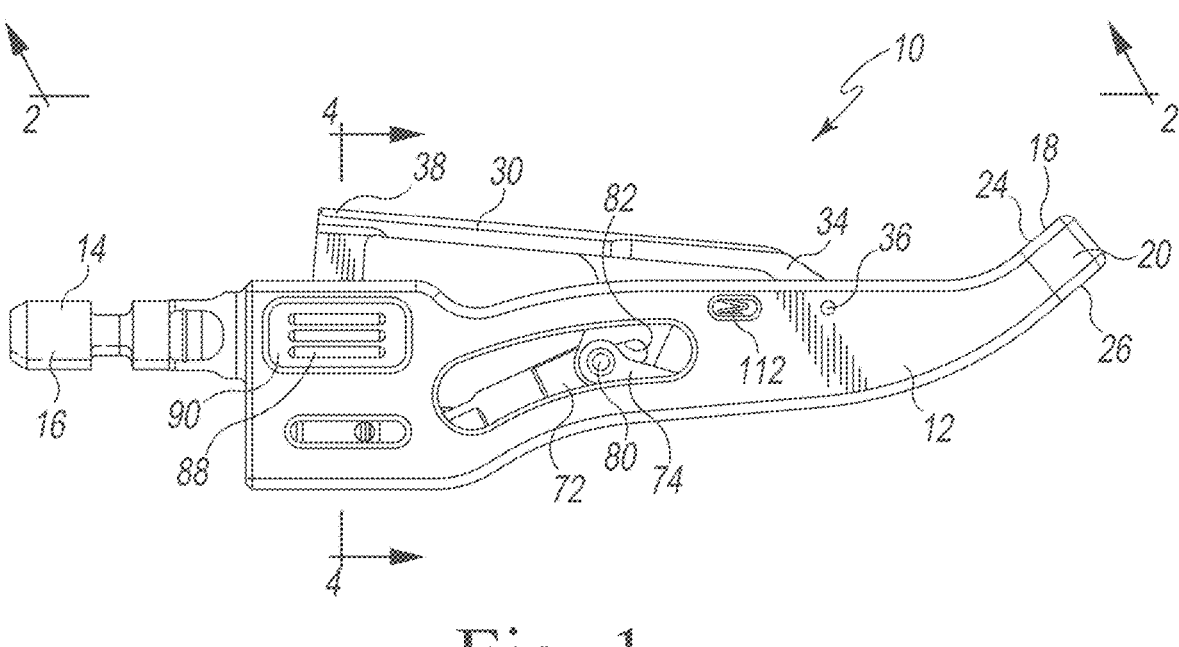
FIG. 1 is a side elevational view of a femoral stem extraction instrument for use in an orthopaedic surgical hip replacement procedure on a patient's femur.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. Additionally, it is to be understood that terms such as top, bottom, front, rear, side, height, length, width, upper, lower, and the like that may be used herein merely describe points of reference and do not necessarily limit embodiments of the present disclosure to any particular orientation or configuration.

Referring now to FIGS. 1-4, an adapter for use with an automated surgical impactor in the form of a femoral stem extraction instrument 10 is shown. The stem extraction instrument 10 is an orthopaedic surgical instrument; that is, a surgical tool used by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. As described further below, the stem extraction instrument 10 is used with an automated surgical impactor to extract a previously implanted femoral stem component from a patient's femur.

Figure 2:
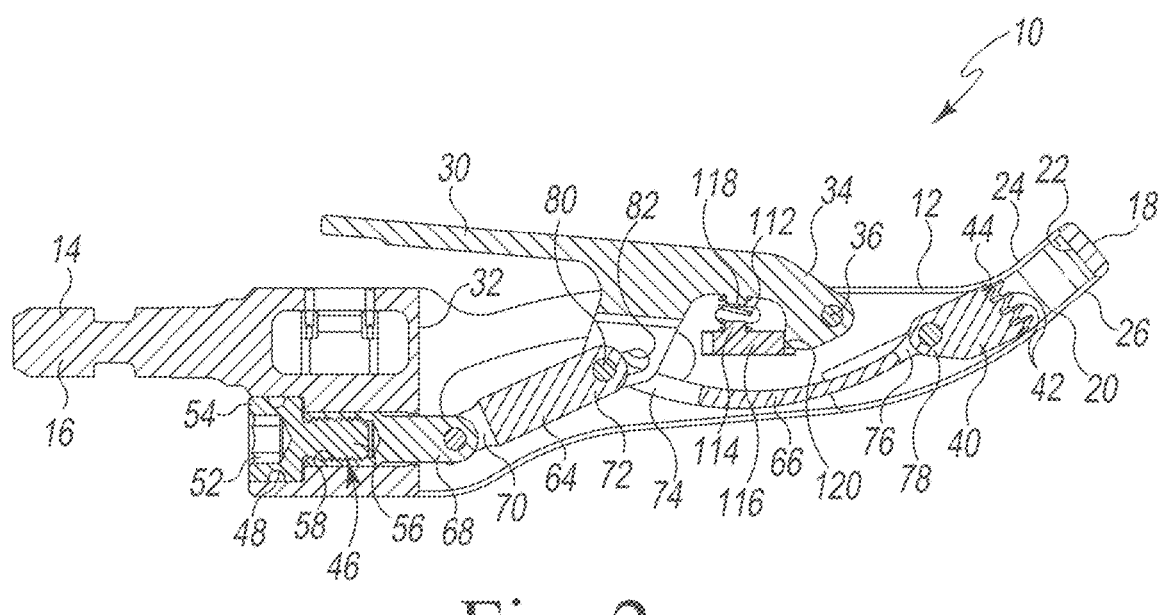
FIG. 2 is a cross sectional view of the femoral stem extraction instrument of FIG. 1 taken along the line 2-2 of FIG. 1, as viewed in the direction of the arrows.
Figure 3:
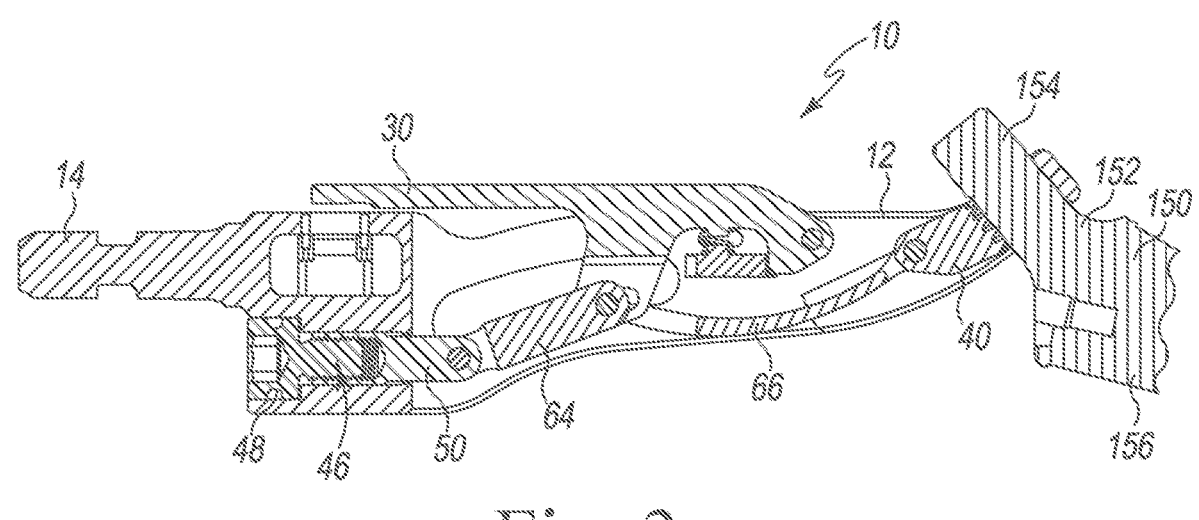
FIG. 3 is a similar view to FIG. 2, but showing the femoral stem extraction instrument secured to the neck of a femoral stem component.

As shown in FIGS. 1-4, the stem extraction instrument 10 includes an elongated body 12 having a connector 14 formed in its proximal end 16. The connector 14 is configured to fit into the chuck of an automated surgical impactor (see FIG. 6). As shown best in FIGS. 2 and 3, an extraction loop 18 is formed in the distal end 20 of the instrument's elongated body 12. The extraction loop 18 has an open-sided bore 22 that extends through the elongated body 12 from its upper surface 24 to its lower surface 26. As shown in FIG. 3, the extraction loop 18 is configured to receive, and thereafter capture, the neck 152 of a femoral stem component 150 therein.

The stem extraction instrument 10 also includes an elongated locking lever 30 that extends outwardly from the inner cavity of the elongated body 12 through an opening 32 formed in the upper surface 24 of the elongated body 12. The locking lever 30 includes a pivot end 34 that is pivotally coupled to the elongated body 12 via a pivot pin 36. As will be described below, an opposite, latch end 38 of the locking lever 30 is selectively captured by a pushbutton latch to retain the locking lever 30 in its locked position.

As shown in FIGS. 2 and 3, a clamping jaw 40 is slidably coupled to the elongated body 12. The clamping jaw 40 includes a number of serrations 42 on its distal end 44. The serrations 42 facilitate a secure connection to the outer surface of the neck 152 of a femoral stem component 150. It should be appreciated that the surfaces of the extraction loop 18 defining the bore 22 may also have similar serrations, or other texturing structures, formed therein. The clamping jaw 40 is configured to slide back and forth in a direction toward and a direction away from the extraction loop 18. Specifically, the clamping jaw 40 is movable between a clamped position and in which the clamping jaw is extended toward the extraction loop 18 and a released position in which the clamping jaw 40 is retracted away from the extraction loop 18. When the clamping jaw 40 is positioned in its clamped position, its serrated distal end 44 is urged into contact with the neck 152 of the femoral stem component 150 so as to assert a clamping force thereon. Such a clamping force captures the neck 152 of the femoral stem component 150 in the extraction loop 18 by virtue of clamping the stem's neck 152 between the clamping jaw 40 and the extraction loop 18. Oppositely, when the clamping jaw 40 is positioned in its released position, the clamping jaw 40 is retracted in a direction away from the extraction loop 18 thereby releasing the neck 152 of the femoral stem component 150.

As shown in FIGS. 2 and 3, a threaded drive assembly 46 is operatively coupled to the clamping jaw 40 and is operable to move the clamping jaw 40 between its clamped position and its released position. Specifically, as seen in FIGS. 2 and 3, the threaded drive assembly 46 includes a drive screw 48 and a drive link 50. The drive screw 48 is rotatably coupled to the elongated body 12 and includes a socket 52 defined in its proximal end 54. A threaded shaft 56 extends distally away from the socket 52. The drive link 50 is slidably coupled to the elongated body 12 so as to be movable within the elongated body 12 in a direction toward, and a direction away from, the extraction loop 18. The drive link 50 has a threaded bore 58 formed therein. The threaded shaft 56 of the drive screw 48 is threadingly received into the threaded bore 58 of the drive link 50. Rotation of the threaded shaft 56 of the drive screw 48 within the threaded bore 58 of the drive link 50 causes linear movement of the drive link 50 within the elongated body 12.

Figure 5:
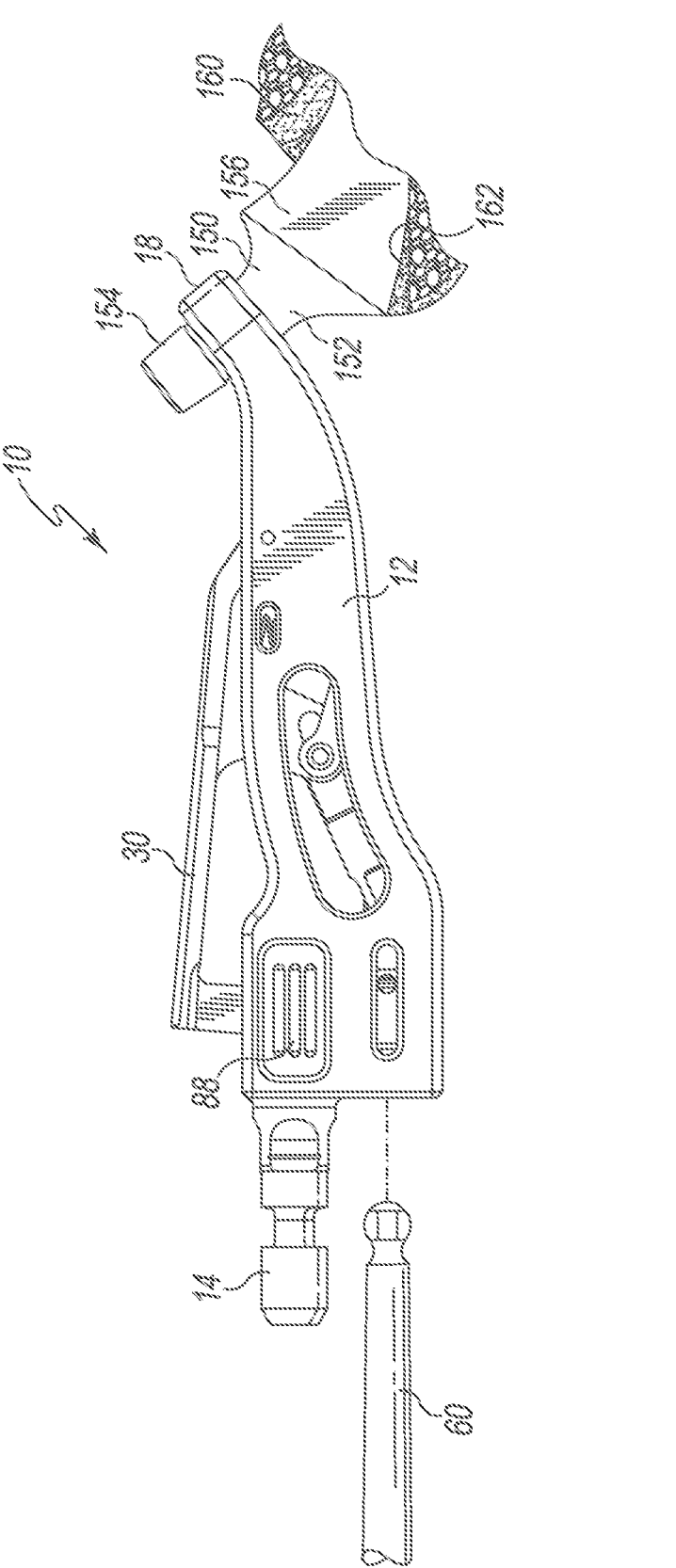
FIG. 5 is a cross-sectional view of a patient's femur during a hip replacement surgical procedure, showing a surgeon preparing to extract an implanted femoral stem component by use of the stem extraction instrument of FIGS. 1-4.

As can be seen in FIGS. 2, 3, and 5, the socket 52 is configured as a hex socket configured to receive a manual or powered ball-end hex driver 60. When a surgeon or other personnel rotates the drive screw 48, the drive screw's threaded shaft 56 is likewise rotated thereby causing linear movement of the drive link 50. Rotation in one direction (e.g., clockwise) moves the drive link 50 and hence the clamping jaw 40 in the direction toward the extraction loop 18 thereby moving the clamping jaw 40 into its clamped position in which the neck 152 of the femoral stem component 150 is captured in the extraction loop 18. Rotation in the opposite direction (e.g., counterclockwise) moves the drive link 50 and hence the clamping jaw 40 in the direction away from the extraction loop 18 thereby moving the clamping jaw 40 into its released position in which the neck 152 of the femoral stem component 150 is released from the extraction loop 18.

As can be seen in FIGS. 2 and 3, the drive link 50 is coupled to the clamping jaw 40 by a linkage that includes a connecting link 64 and a leaf spring 66. In particular, the distal end 68 of the drive link 50 is pivotally coupled to the proximal end 70 of the connecting link 64, with the connecting link's opposite distal end 72 being coupled to the proximal end 74 of the leaf spring 66. The opposite distal end 76 of the leaf spring 66 is pivotally coupled to the proximal end 78 of the clamping jaw 40. As shown in FIGS. 2 and 3, the connecting link 64 and the leaf spring 66 are both coupled to the locking lever 30. Specifically, the pivot pin 80 coupling the connecting link's distal end 72 to the leaf spring's proximal end 74 is captured in an arcuate-shaped slot 82 formed in the locking lever 30. As the drive link 50 is driven within the elongated body 12 in a direction toward, and a direction away from, the extraction loop 18, the pivot pin 80 translates within the locking lever's slot 82 in a similar direction.

The leaf spring 66 is utilized to put a fixating load in the form of a spring bias on the neck 152 of the femoral stem component 150 thereby creating a rigid construct during extraction of the stem component 150. Such a fixating load is applied and removed by use of the locking lever 30. In particular, the locking lever 30 is movable between an unlocked position (as shown in FIGS. 1 and 2) in which the latch end 38 of the locking lever 30 is extended away from the elongated body 12 and a locked position (as shown in FIG. 3) in which the latch end 38 is positioned proximate to the elongated body 12 and captured by a pushbutton catch 88. When the locking lever 30 is positioned in its unlocked position, the leaf spring 66 is relaxed and thus does not exert a spring bias on the clamping jaw 40 (and hence the neck 152 of the femoral stem component 150). However, as the locking lever 30 is moved to its locked position, the leaf spring 66 is compressed thereby exerting a spring bias on the clamping jaw 40 (and hence the neck 152 of the femoral stem component 150).

Figure 6:
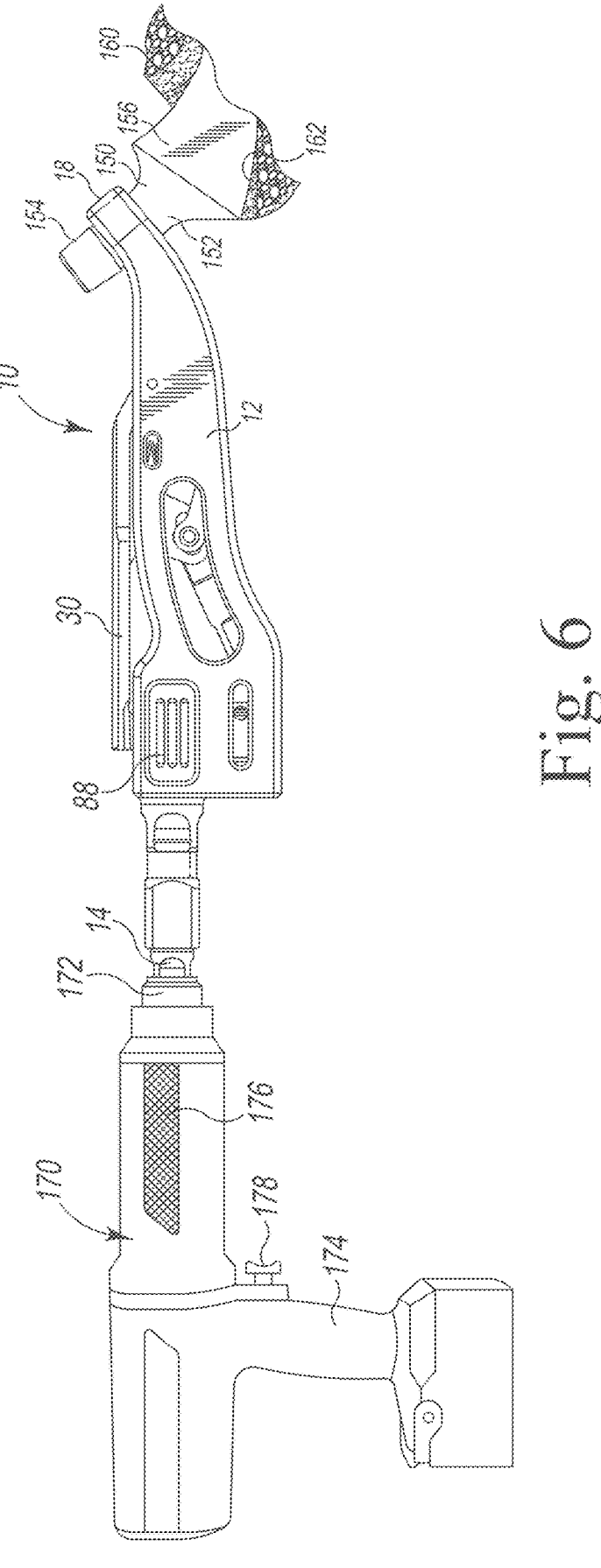
FIG. 6 is a view similar to FIG. 5, but showing the stem extraction instrument fully secured to the implanted femoral stem component and coupled to an automated surgical impactor.

As alluded to above, the pushbutton catch 88 may be used to selectively retain the locking lever 30 in the locked position shown in FIGS. 3 and 6. The pushbutton catch 88 includes a button surface 90 positioned generally flush with the outer side surface of the elongated body 12. The button surface 90 is configured to be pressed by a surgeon and thus may be grooved or otherwise textured to provide enhanced grip.

Figure 4:
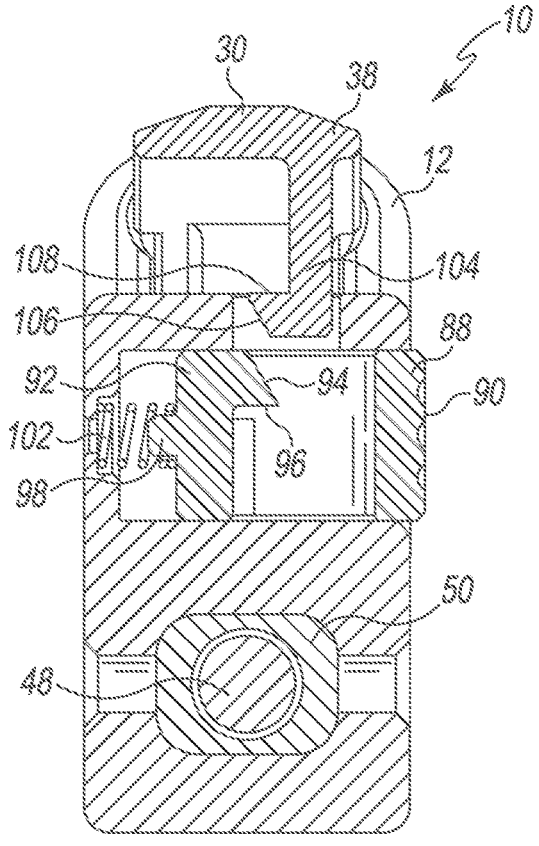
FIG. 4 is a cross sectional view of the femoral stem extraction instrument of FIG. 1 taken along the line 4-4 of FIG. 1, as viewed in the direction of the arrows.

As shown in FIG. 4, the pushbutton catch 88 also includes a locking pawl 92 that includes a ramp-shaped upper cam surface 94 and a lower surface 96. A guide post 98 extends from a back surface of the locking pawl 92 toward an inner surface of the elongated body 12. A compression spring 102 is captured around the guide post 98 and thereby retained between the inner surface of the elongated body 12 and the back surface of the locking pawl 92. The spring 102 urges against the inner surface of the elongated body 12 and the back surface of the locking pawl 92 so as to bias the pushbutton catch 88 toward the outer surface of the elongated body 12 (i.e., the compression spring 102 urges the pushbutton catch 88 rightwardly as viewed in the orientation of FIG. 4).

As shown in FIG. 4, the latch end 38 of the locking lever 30 has a downwardly extending latch 104 formed therein. The latch 104 has a ramp-shaped lower cam surface 106 and an upper surface 108 formed therein. When the locking lever 30 is in the locked position, the upper surface 108 of the latch 104 engages the lower surface 96 of the locking pawl 92 thereby retaining the latch 104. When the surgeon or other personnel depresses the button surface 90, the pushbutton catch 88 slides toward the opposite inner surface of elongated body 12 (i.e., it slides leftwardly as viewed in the orientation of FIG. 4), and the lower surface 96 of the locking pawl 92 slides off the upper surface 108 of the latch 104 thereby releasing the locking lever 30. As can be seen in FIG. 2, a compression spring 112 biases the locking lever 30 into its unlocked position. Thus, when the latch 104 is released by pressing the pushbutton catch 88, the latch end 38 of the locking lever 30 is urged toward its unlocked position by the spring bias of the compression spring 112, which releases tension on the leaf spring 66.

When a surgeon or other user moves the lever 30 from its unlocked position to its locked position without depressing the pushbutton catch 88, the lower cam surface 106 of the latch 104 engages the upper cam surface 94 of the locking pawl 92. This engagement of the cam surfaces 94, 106 overcomes the spring bias of the compression spring 102 and forces the pushbutton catch 88 to slide toward the opposite inner surface of elongated body 12 (i.e., it slides leftwardly as viewed in the orientation of FIG. 4). When the latch 104 passes the pawl 90 and the cam surfaces 94, 106 disengage, the spring 102 forces the pushbutton catch 88 to slide back toward its original position (i.e., the compression spring 102 urges the pushbutton catch 88 rightwardly as viewed in the orientation of FIG. 4), which causes the upper surface 108 of the latch 104 to engage the lower surface 96 of the locking pawl 92 thereby retaining the latch 104.

As described above, use of the pushbutton catch 88 provides a positive lock on the locking lever 30 thereby preventing inadvertent release of the locking lever 30 during use of the stem extraction instrument 10. Moreover, the location of the pushbutton catch 88 in the elongated body 12 allows the locking lever 30 to be opened and/or closed by the surgeon using a single hand.

As can be seen in FIGS. 2 and 3, the lower end of the compression spring 112 that biases the locking lever 30 into its unlocked position is captured on a post 114 formed in a plate 116 defined in the elongated body 12 with the opposite, upper end of the compression spring 112 being captured on a similarly-shaped post 118 formed in a lower surface of the locking lever 30. A distal edge 120 of the plate 116 functions as a built-in stop which prevents over-tightening thereby preventing damage to the leaf spring 66.

In the illustrative embodiment, the stem extraction instrument 10 is formed from a metallic material such as, for example, stainless steel. In particular, the elongated body 12, the locking lever 30, and the various internal components form an assembled metallic instrument. The stem extraction instrument 10 may be formed by conventional machining techniques, or alternatively, by the use of 3-D printing technology. In the case of 3-D printing, the stem extraction instrument 10 is formed in a layer-by-layer fashion.

In use, the femoral extraction instrument 10 may be used by a surgeon to extract an implanted femoral stem component 150 from the intramedullary canal 162 of a patient's femur 160 during a hip replacement surgical procedure such as a revision hip replacement surgical procedure. Prior to extraction of the femoral stem component 150, the surgeon performs a number of intra-operative surgical steps to gain access to the implanted femoral stem component 150. The surgeon also removes the femoral head component (not shown) from the implanted femoral stem component's trunnion 154. Thereafter, as shown in FIGS. 5 and 6, the surgeon advances the stem extraction instrument 10 into the surgical site and positions the instrument's extraction loop 18 around the neck 152 of the femoral stem component 150 at a location between its trunnion 154 and its proximal body 156.

Thereafter, the surgeon uses a manual or powered ball-end hex driver 60 to operate the threaded drive assembly 46 to clamp the neck 152 of the femoral stem component 150 within the extraction loop 18. Specifically, the surgeon rotates the drive screw 48 in a direction (e.g., clockwise) that moves the drive link 50 and hence the clamping jaw 40 in the direction toward the extraction loop 18 thereby moving the clamping jaw 40 into its clamped position in which the neck 152 of the femoral stem component 150 is securely captured (i.e., clamped) within the extraction loop 18.

As shown in FIG. 6, once the neck 152 of the femoral stem component 150 is secured within the extraction loop 18, the surgeon moves the locking lever 30 into its locked position to apply a fixating load on the clamped femoral stem component 150. Specifically, the surgeon squeezes the stem extraction instrument 10 so as to urge the locking lever 30 into its locked position in which its latch 104 is captured and retained by the pushbutton catch 88. Doing so compresses the leaf spring 66 which asserts a fixating load in the form of a spring bias on the neck 152 of the femoral stem component 150 thereby creating a rigid construct of the instrument 10 and the stem component 150.

Thereafter, the instrument's connector 14 is coupled to the chuck 172 of an automated surgical impactor 170 (see FIG. 6). The automated surgical impactor 170 may be embodied as a Kincise™ surgical automated system commercially available from DePuy Synthes of Warsaw, Indiana. In the illustrative embodiment, the automated surgical impactor 170 includes a chuck 172 in the form of a twist-lock collar. The automated surgical impactor 170 also includes a primary hand grip 174, a secondary hand grip 176, and a trigger 178. Once the chuck 172 has been coupled to the connector 14 of the stem extraction instrument 10, the surgeon depresses the trigger 178, which causes the automated surgical impactor 170 to generate an extraction force in the form of a series of controlled percussive impacts on the stem extraction instrument 10. The stem extraction instrument 10 communicates the extraction force from those percussive impacts to the implanted femoral stem component 150 thereby allowing the component 150 to be extracted from the intramedullary canal 162 of the patient's femur 160. During such an extraction, the surgeon's hands may remain on the automated surgical impactor 170 since the pushbutton catch 88 maintains the locking lever 30 in its locked position. Additionally, the leaf spring 66 retains the femoral stem component 150 rigidly secured to the stem extraction instrument 10 during impaction. Unlike adapters using a typical rigid drive train attachment mechanism, the compliant, flexible leaf spring 66 of the stem extraction instrument 10 may not back out or otherwise loosen during impaction, even when subject to frequent, lower-amplitude impactions generated by the automated surgical impactor 170.

Once the surgeon has extracted the femoral stem component 150 from the intramedullary canal 162 of the patient's femur 160, the connector 14 of the stem insertion instrument 10 may be decoupled from the chuck 172 of an automated surgical impactor 170. The surgeon or other personnel may then depress the button surface 90 of the pushbutton catch 88 so as to release the locking lever 30 thereby causing the locking lever 30 to be automatically moved to its unlocked position (by the spring bias asserted on it). The surgeon or other personnel then rotates the drive screw 48 in a direction (e.g., counterclockwise) that moves the drive link 50 and hence the clamping jaw 40 in the direction away from the extraction loop 18 thereby moving the clamping jaw 40 into its released position in which the neck 152 of the femoral stem component 150 is released from the extraction loop 18. Thereafter, the surgeon performs the remaining steps in the surgical procedure.

Figure 7:
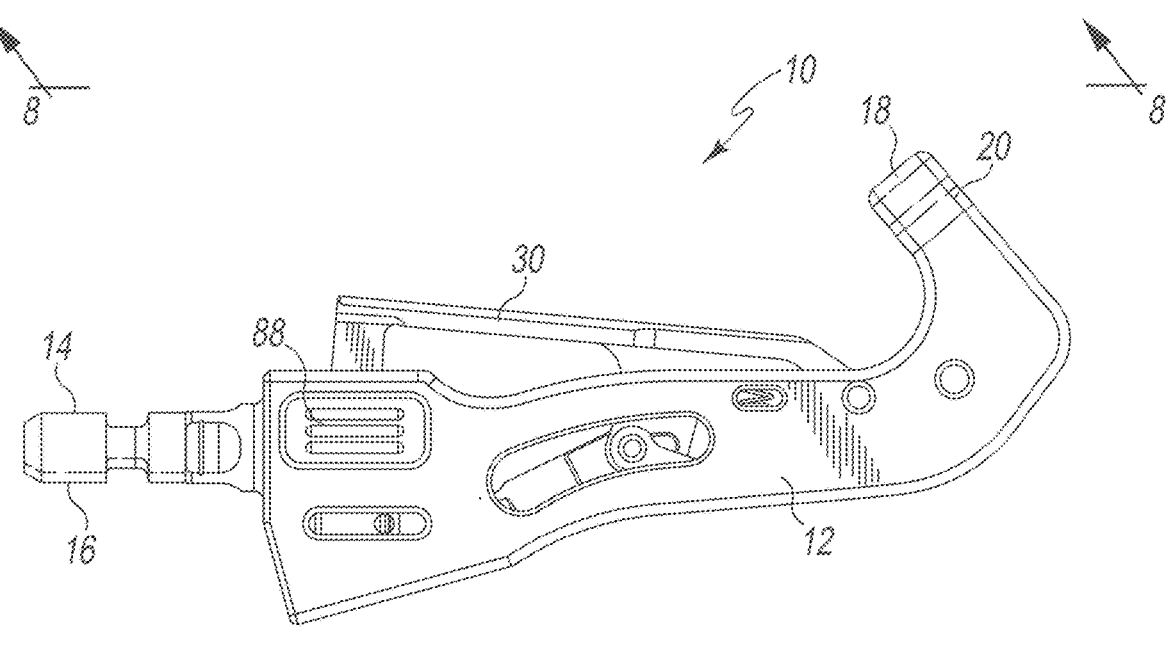
FIGS. 7 and 8 are views similar to FIGS. 1 and 2, respectively, but showing another embodiment of a stem extraction instrument.
Figure 8:
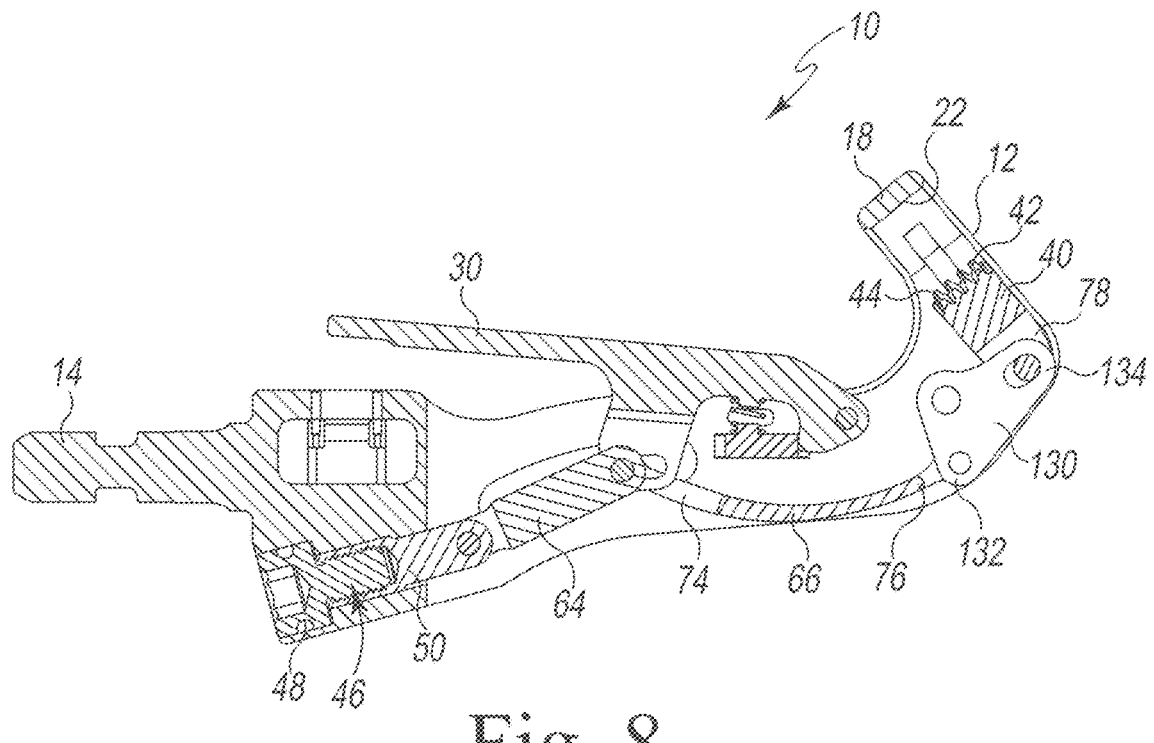

Referring now to FIGS. 7 and 8, there is shown another embodiment of the stem extraction instrument 10. The stem extraction instrument 10 of FIGS. 7 and 8 is essentially the same as the instrument of FIGS. 1-6 except for the certain features which have been modified to enhance the instrument's use in a direct anterior approach hip replacement surgical procedure. Specifically, when using the direct anterior approach, the surgeon does not have line-of-sight access to the intramedullary canal of the patient's femur. This limited access and visibility makes it difficult for the surgeon to navigate "around the corner" of the proximal end of the patient's femur 160. As such, the distal end 20 of the elongated body 12 of the stem extraction instrument 10 of FIGS. 7 and 8 has been modified to include curved outer surfaces so as to medially offset the extraction loop 18 relative to the instrument 10 of FIGS. 1-6.

As shown in FIG. 8, to accommodate the modified shape of its elongated body 12, the stem extraction instrument 10 of FIGS. 7 and 8 includes a knuckle link 130 pivotally coupled to the elongated body 12. The knuckle link 130 translates the linear movement generated by the threaded drive assembly 46 and the spring bias generated by leaf spring 66 around the curved shape of the elongated body 12. Specifically, the distal end 76 of the leaf spring 66 is pivotally coupled to the proximal end 132 of the knuckle link 130, with the distal end 134 of the knuckle link 130 being coupled to the proximal end 78 of the clamping jaw 40 by virtue of capturing a pin formed in the clamping jaw 40 within a slot formed in the knuckle link's distal end 134. As such, movement of the leaf spring 66 by the threaded drive assembly 46 is translated to the clamping jaw 40 through the knuckle link 130. Similarly, the spring bias generated by the leaf spring 66 is likewise translated to the clamping jaw 40 through the knuckle link 130.

Figure 9:
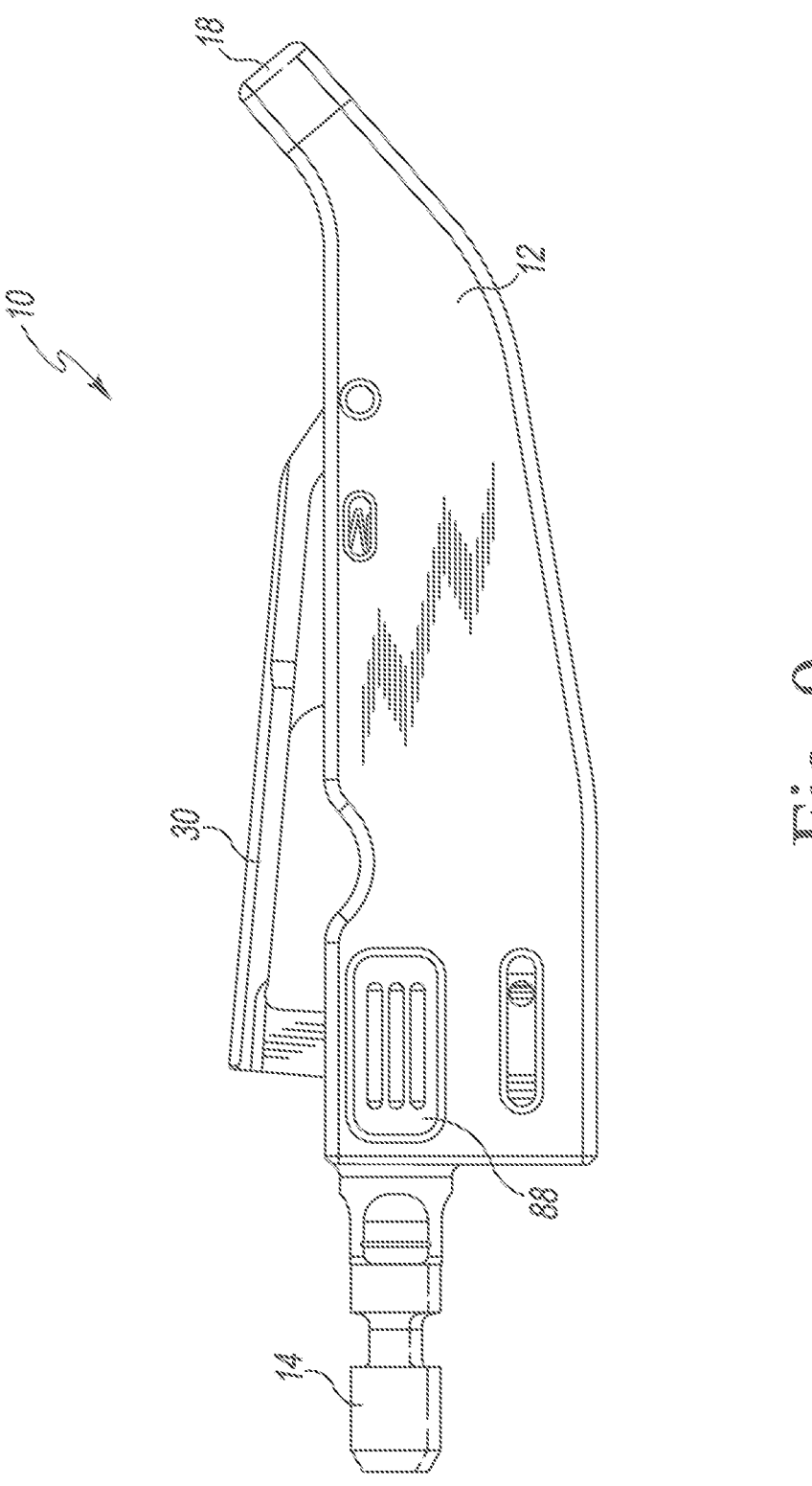
FIG. 9 is a view similar to FIG. 1, but showing yet another embodiment of a stem extraction instrument.
Figure 10:
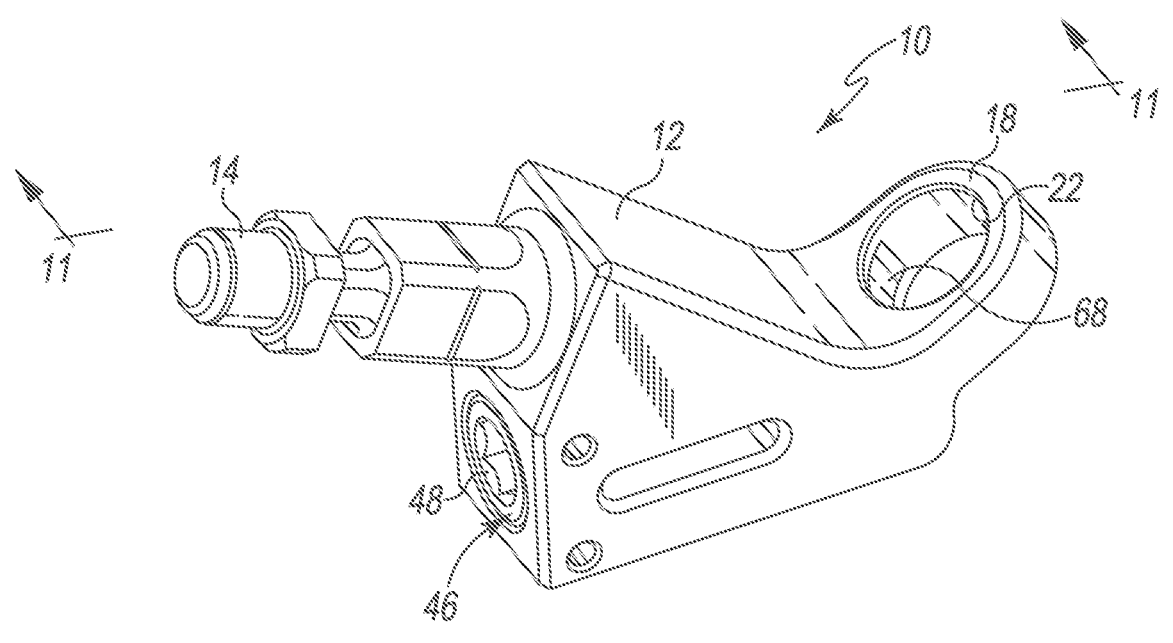
FIG. 10 is a perspective view of another embodiment of a stem extraction instrument.
Figure 11:
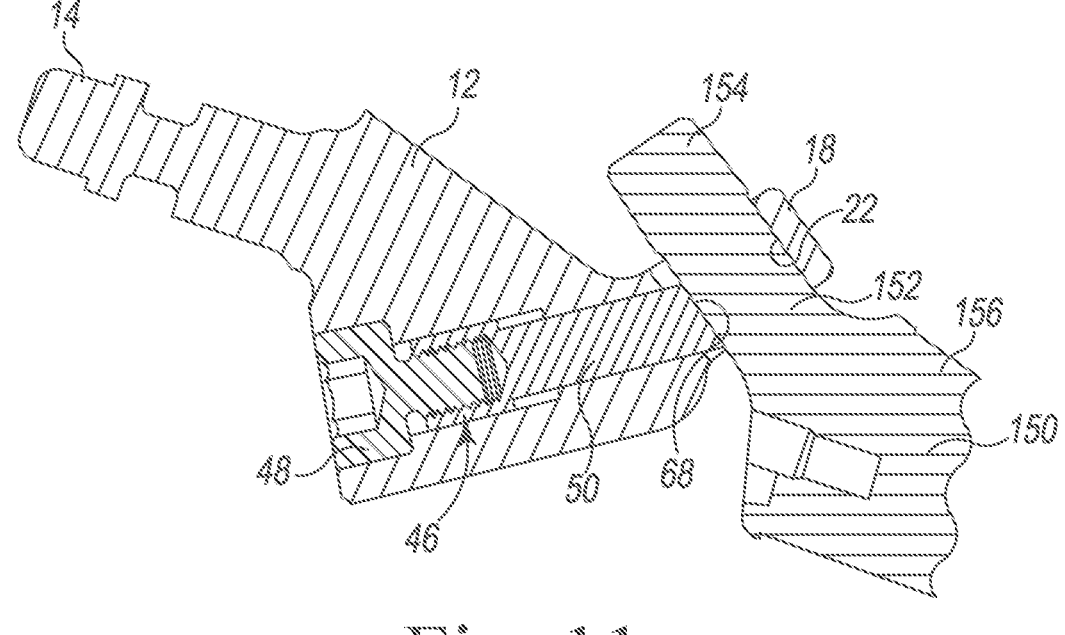
FIG. 11 is a cross sectional view of the femoral stem extraction instrument of FIG. 10 taken along the line 11-11 of FIG. 10, as viewed in the direction of the arrows, note the femoral stem extraction instrument is shown secured to the neck of a femoral stem component in FIG. 11.

Referring now to FIGS. 9-11, additional embodiments of the stem extraction instrument 10 are shown. For example, the stem extraction instrument 10 of FIG. 9 is essentially the same as the instrument of FIGS. 1-6 except the windows in the elongated body 12 have been removed. In regard to the embodiment of FIGS. 10 and 11, certain structures of the instrument 10 have been removed to produce a somewhat "reduced-feature" design. In particular, the stem extraction instrument of FIGS. 10-11 does not include the leaf spring 66 and locking lever 30 for applying a fixating load to the neck 152 of the femoral stem component 150. Instead, the distal end 68 of the drive link 50 has been modified to clamp directly on the neck 152 of the femoral stem component 150. As such, operation of the threaded drive assembly 46 causes the drive link 50 to be urged into, and out of, contact with the neck 152 of the femoral stem component 150 so as to selectively capture the femoral stem component 150 in the instrument's extraction loop 18.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, although the concepts of the present disclosure have been described in regard to an orthopaedic surgical instrument for use with an automated surgical impactor, and has significant advantages thereby, certain of such advantages may be recognized in other instrument designs. For instance, the concepts of the present disclosure may be utilized in the design of an orthopaedic surgical instrument that is manually impacted with a surgical mallet or hammer.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for extracting a femoral stem component during an orthopaedic hip replacement surgical procedure on a patient's femur, the orthopaedic surgical instrument comprising:

an elongated body having (i) a connector formed in a proximal end of the elongated body, the connector being configured to fit into a chuck of an automated surgical impactor, and (ii) an extraction loop formed in a distal end of the elongated body, the extraction loop has a bore that extends through the elongated body and is configured to receive a neck of the femoral stem component therein, a locking lever having a pivot end pivotally coupled to the elongated body and an opposite latch end, a clamping jaw slidably coupled to the elongated body, the clamping jaw being movable between (i) a clamped position in which the clamping jaw is extended toward the extraction loop, and (ii) a released position in which the clamping jaw is retracted away from the extraction loop, a threaded drive assembly operatively coupled to the clamping jaw, the threaded drive assembly being operable to move the clamping jaw between its clamped position and its released position, and a leaf spring having a first end pivotally coupled to the locking lever and a second end coupled to the clamping jaw, wherein the threaded drive assembly includes a connecting link coupled to the first end of the leaf spring with a pivot pin, the connecting link being pivotally coupled to the locking lever via the pivot pin.

2. The orthopaedic surgical instrument of claim 1, wherein the threaded drive assembly comprises a drive screw rotatably coupled to the elongated body and a drive link slidably coupled to the elongated body, wherein:

the drive link is operatively coupled to the clamping jaw, the drive screw has a socket defined in its proximal end and a threaded shaft extending distally away from the socket, the drive link has a threaded bore formed therein, the threaded shaft of the drive screw is positioned in the threaded bore of the drive link, rotation of the drive screw in a first direction causes the drive link to be moved in the direction toward the extraction loop, and rotation of the drive screw in a second, opposite direction causes the drive link to be moved in the direction away from the extraction loop.

3. The orthopaedic surgical instrument of claim 1, further comprising a pushbutton catch coupled to the elongated body, wherein the locking lever is movable between an unlocked position in which the latch end is spaced apart from the elongated body and a locked position in which the latch end is captured by the pushbutton catch.

4. The orthopaedic surgical instrument of claim 3, further comprising a compression spring positioned between the locking lever and the elongated body, the compression spring biases the locking lever into its unlocked position.

5. The orthopaedic surgical instrument of claim 3, wherein the leaf spring asserts a spring bias on the neck of the femoral stem component when the neck of the femoral stem component is positioned in the extraction loop and the locking lever is positioned in its locked position.

6. The orthopaedic surgical instrument of claim 1, wherein the clamping jaw asserts a clamping force on the neck of the femoral stem component when the neck of the femoral stem component is positioned in the extraction loop and the clamping jaw is positioned in its clamped position.

7. The orthopaedic surgical instrument of claim 1, wherein the second end of the leaf spring is pivotally coupled to the clamping jaw.

8. The orthopaedic surgical instrument of claim 1, further comprising a knuckle link pivotally coupled to the elongated body, wherein:

the second end of the leaf spring is pivotally coupled to a first end of the knuckle link, and a second end of the knuckle link is coupled to the clamping jaw.

9. The orthopaedic surgical instrument of claim 1, wherein the locking lever has a slot formed therein, and wherein the pivot pin is located in the slot to translate within the slot in the direction toward, and the direction away from, the extraction loop.

10. The orthopaedic surgical instrument of claim 1, wherein the locking lever has a connection point located between the pivot end and the latch end thereof, and the first end of the leaf spring and the connecting link are coupled to the locking lever at the connection point.

11. An orthopaedic surgical instrument for extracting a femoral stem component during an orthopaedic hip replacement surgical procedure on a patient's femur, the orthopaedic surgical instrument comprising:

an elongated body having (i) a connector formed in a proximal end of the elongated body, the connector being configured to fit into the chuck of an automated surgical impactor, and (ii) an extraction loop formed in a distal end of the elongated body, the extraction loop has a bore that extends through the elongated body and is configured to receive a neck of the femoral stem component therein, a locking lever having a pivot end pivotally coupled to the elongated body and an opposite latch end, a drive link slidably coupled to the elongated body, the drive link being movable within the elongated body in a direction toward, and a direction away from, the extraction loop, a connecting link having a first end pivotally coupled to the locking lever and a second end pivotally coupled to the drive link, a clamping jaw slidably coupled to the elongated body, the clamping jaw being movable between (i) a clamped position in which the clamping jaw is extended toward the extraction loop, and (ii) a released position in which the clamping jaw is retracted away from the extraction loop, and a leaf spring having a first end pivotally coupled to the locking lever and a second end coupled to the clamping jaw, wherein (i) movement of the drive link in the direction toward the extraction loop causes the clamping jaw to be positioned in its clamped position, and (ii) movement of the drive link in the direction away from the extraction loop causes the clamping jaw to be positioned in its released position.

12. The orthopaedic surgical instrument of claim 11, further comprising a drive screw rotatably coupled to the elongated body, wherein:

the drive screw has a socket defined in its proximal end and a threaded shaft extending distally away from the socket, the drive link has a threaded bore formed therein, the threaded shaft of the drive screw is positioned in the threaded bore of the drive link, rotation of the drive screw in a first direction causes the drive link to be moved in the direction toward the extraction loop, and rotation of the drive screw in a second, opposite direction causes the drive link to be moved in the direction away from the extraction loop.

13. The orthopaedic surgical instrument of claim 11, wherein:

the locking lever has a slot formed therein, and the first end of the leaf spring and the first end of the connecting link are coupled to one another by a pivot pin that translates within the slot of the locking lever.

14. The orthopaedic surgical instrument of claim 11, further comprising a pushbutton catch coupled to the elongated body, wherein the locking lever is movable between an unlocked position in which the latch end is spaced apart from the elongated body and a locked position in which the latch end is captured by the pushbutton catch.

15. The orthopaedic surgical instrument of claim 14, further comprising a compression spring positioned between the locking lever and the elongated body, the compression spring biases the locking lever into its unlocked position.

16. The orthopaedic surgical instrument of claim 14, wherein the leaf spring asserts a spring bias on the neck of the femoral stem component when the neck of the femoral stem component is positioned in the extraction loop and the locking lever is positioned in its locked position.

17. The orthopaedic surgical instrument of claim 11, wherein the clamping jaw asserts a clamping force on the neck of the femoral stem component when the neck of the femoral stem component is positioned in the extraction loop and the clamping jaw is positioned in its clamped position.

18. The orthopaedic surgical instrument of claim 11, wherein the second end of the leaf spring is pivotally coupled to the clamping jaw.

19. The orthopaedic surgical instrument of claim 11, further comprising a knuckle link pivotally coupled to the elongated body, wherein:
    the second end of the leaf spring is pivotally coupled to a first end of the knuckle link, and
    a second end of the knuckle link is coupled to the clamping jaw.

\* \* \* \* \*